(12) United States Patent
Kanegae et al.

(10) Patent No.: US 7,838,818 B2
(45) Date of Patent: Nov. 23, 2010

(54) LIGHT-STIMULUS ILLUMINATION APPARATUS WHICH SCANS LIGHT-STIMULUS LASER LIGHT IN A DIRECTION INTERSECTING AN OPTICAL AXIS

(75) Inventors: Shigeru Kanegae, Ina (JP); Tatsuo Nakata, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/811,792

(22) Filed: Jun. 12, 2007

(65) Prior Publication Data
US 2007/0295892 A1 Dec. 27, 2007

(30) Foreign Application Priority Data
Jun. 22, 2006 (JP) ............... 2006-172898

(51) Int. Cl.
H01J 3/14 (2006.01)
H01J 40/14 (2006.01)
G01J 1/32 (2006.01)

(52) U.S. Cl. .................... 250/235; 250/214 R; 250/205

(58) Field of Classification Search ............ 250/201.3, 250/235, 236, 458.1, 462.1, 306, 307, 205, 250/214 R; 359/368, 385, 389, 196–202, 359/204, 205–226, 285, 305; 356/318, 311, 356/337, 338, 343
See application file for complete search history.

(56) References Cited

U.S. PATENT DOCUMENTS

| 6,031,225 | A | * | 2/2000 | Stern et al. ............... 250/235 |
| 6,094,300 | A | | 7/2000 | Kashima et al. |
| 6,433,929 | B1 | * | 8/2002 | Sasaki .................. 359/388 |
| 6,963,398 | B2 | * | 11/2005 | Sasaki et al. ............ 356/318 |
| 2002/0141051 | A1 | * | 10/2002 | Vogt et al. .............. 359/385 |
| 2002/0149769 | A1 | | 10/2002 | Roorda et al. |
| 2003/0156323 | A1 | | 8/2003 | Overbeck |
| 2005/0122579 | A1 | * | 6/2005 | Sasaki .................. 359/385 |
| 2006/0071143 | A1 | | 4/2006 | Saggau et al. |
| 2006/0250689 | A1 | * | 11/2006 | Ulrich et al. ............ 359/385 |
| 2007/0201123 | A1 | | 8/2007 | Saggau et al. |

* cited by examiner

Primary Examiner—Que T Le
Assistant Examiner—Pascal M Bui-Pho
(74) Attorney, Agent, or Firm—Holtz, Holtz, Goodman & Chick, PC

(57) ABSTRACT

The invention provides a light-stimulus illumination apparatus comprising a light source for emitting light-stimulus laser light; a scanning unit including at least one acousto-optic device for scanning the light-stimulus laser light emitted from the light source in a direction intersecting an optical axis; and a control unit for controlling the scanning unit. The control unit controls the scanning unit so that the light-stimulus laser light irradiates a plurality of spatially separated regions in a time-division manner.

8 Claims, 5 Drawing Sheets

LIGHT-STIMULUS ILLUMINATION APPARATUS WHICH SCANS LIGHT-STIMULUS LASER LIGHT IN A DIRECTION INTERSECTING AN OPTICAL AXIS

BACKGROUND OF THE INVENTION

1. Field of the Invention

The present invention relates to a light-stimulus illumination apparatus.

This application is based on Japanese Patent Application No. 2006-172898, the content of which is incorporated herein by reference.

2. Description of Related Art

A conventionally known microscope apparatus including a light-stimulus illumination apparatus is disclosed, for example, in U.S. Pat. No. 6,094,300.

The light-stimulus illumination apparatus in this microscope apparatus includes a light source for emitting light-stimulus laser light and a galvanometer mirror for two-dimensionally scanning the light-stimulus laser light emitted from the light source.

The galvanometer mirror, however, adjusts the scanning position of the light-stimulus laser light by adjusting the rotation angle of a mirror. Therefore, when applying the light stimulus to regions that are separated from each other, some time is required to move from one region to another region.

In addition, the scanning of the light-stimulus laser light by the galvanometer mirror is performed continuously by the rotary operation of the galvanometer mirror. Therefore, when applying the light stimulus to regions that are separated from each other, the light-stimulus laser light is unavoidably radiated in areas between these regions while moving from one region to another region. In order to prevent this, it is necessary to provide a device for quickly turning the light-stimulus laser light on and off.

BRIEF SUMMARY OF THE INVENTION

The present invention provides a light-stimulus illumination apparatus which can apply a light stimulus to a plurality of spatially separated regions within a short period of time.

A first aspect of the present invention is a light-stimulus illumination apparatus comprising a light source configured to emit light-stimulus laser light; a scanning unit including at least one acousto-optic device configured to scan the light-stimulus laser light emitted from the light source in a direction intersecting an optical axis; and a control unit configured to control the scanning unit, wherein the control unit controls the scanning unit so that the light-stimulus laser light irradiates a plurality of spatially separated regions in a time-division manner.

According to this configuration, the light-stimulus laser light emitted from the light source is scanned in a direction intersecting the optical axis by the scanning unit formed of the acousto-optic device. The diffraction angle of the acousto-optic device is instantaneously changed by changing the frequency of the input command signal. Therefore, unlike the case of a galvanometer mirror device in which a mirror is physically rotated, it is possible to instantaneously move the scanning position of the light-stimulus laser light. By controlling the scanning unit with the control unit, it is possible to instantaneously switch the scanning position to a plurality of spatially separated regions and irradiate them with the light-stimulus laser light. Accordingly, when used to observe a fast response of a specimen, it is possible to acquire the desired observation results.

In the light-stimulus illumination apparatus described above, the control unit preferably controls the scanning unit so that the light-stimulus laser light irradiates the plurality of spatially separated regions discontinuously.

With this configuration, it is possible to irradiate a plurality of regions with the light-stimulus laser light to apply a light stimulus, without irradiating the areas between the plurality of spatially separated regions with the light-stimulus laser light. In other words, by switching the frequency of the input command signal, the acousto-optic device can discontinuously move the scanning point to a subsequent region that is spatially separated from a given region. Therefore, the frequencies of the respective command signals are changed within the plurality of spatially separated regions to scan the light-stimulus laser light, and between a given region and the subsequent region, it is possible to make sure that the light-stimulus laser light does not irradiate the specimen by switching the frequency. As a result, it is possible to apply the light stimulus with superior accuracy to only the desired regions. In addition, since the light-stimulus laser light does not irradiate unnecessary regions, it is possible to prevent the occurrence of problems such as fading of the specimen.

In the light-stimulus illumination apparatus described above, the control unit may adjust the amplitude of a command signal input to the acousto-optic device according to a scanning position of the light-stimulus laser light scanned by the scanning unit.

The diffraction angle of the acousto-optic device is changed by changing the frequency of the input command signal, thus changing the scanning position of the light-stimulus laser light. In such a case, unless a countermeasure is taken, changing the diffraction angle changes the diffraction efficiency, which changes the intensity of the emitted light-stimulus laser light. In contrast, according to the present invention, by adjusting the amplitude of the command signal input to the acousto-optic device according to the scanning position, it is possible to adjust the device so that the light-stimulus laser light has a constant intensity independent of the scanning position.

The light-stimulus illumination apparatus described above may further comprise a focal-position adjusting unit configured to change the focal position of the light-stimulus laser light in the optical-axis direction, wherein the control unit controls the focal-position adjusting unit in synchronization with the scanning unit.

With this configuration, by operating the focal-position adjusting unit, it is possible to irradiate a three-dimensional region with the light-stimulus laser light.

In the light-stimulus illumination apparatus described above, the light-stimulus laser light may be ultrashort pulsed laser light.

With this configuration, with high resolution in the optical-axis direction, it is possible to apply a light stimulus to only an extremely thin region in the optical-axis direction.

The light-stimulus illumination apparatus described above may further comprise a light detector configured to detect fluorescence due to multiphoton excitation produced by irradiation with the light-stimulus laser light, without the fluorescence returning to the scanning unit.

With this configuration, it is possible to acquire an observation image using the fluorescence due to multiphoton excitation produced as a result of the light stimulus.

In the light-stimulus illumination apparatus described above, the control unit may control the scanning unit so that the light-stimulus laser light is turned off after completing irradiation of one region and irradiation of a subsequent region is started after a predetermined time has elapsed.

A second aspect of the present invention is a microscope apparatus comprising the light-stimulus illumination apparatus described above.

With this microscope apparatus, it is possible to apply a light stimulus to a plurality of spatially separated regions within an extremely short period of time, and it is thus possible to observe a fast response of the specimen.

A third aspect of the present invention is a laser-scanning microscope apparatus comprising the light-stimulus illumination apparatus described above; and a laser-scanning microscope. The laser-scanning microscope includes an observation light source configured to emit observation laser light; an observation scanning unit configured to two-dimensionally scan the observation laser light on a specimen; an objective lens configured to converge the observation laser light on the specimen and to collect observation light emitted from the specimen by irradiation with the observation laser light; a detection unit configured to detect the observation light collected by the objective lens; and an image-generating unit configured to generate an observation image of the specimen based on a detection signal from the detection unit. The light-stimulus laser light irradiates the specimen via the objective lens of the laser-scanning microscope.

The laser-scanning microscope apparatus described above may further comprise a combining unit, between the observation scanning unit and the objective lens, configured to combine the light-stimulus laser light from the light-stimulus illumination apparatus, wherein the light-stimulus laser light scanned by the scanning unit of the light-stimulus illumination apparatus is guided to the combining unit.

The present invention affords an advantage in that it is possible to apply a light stimulus to a plurality of spatially separated regions within a short period of time.

DETAILED DESCRIPTION OF THE INVENTION

A light-stimulus illumination apparatus and a microscope apparatus according to an embodiment of the present invention will be described below with reference to FIGS. 1 to 3.

Figure 1:
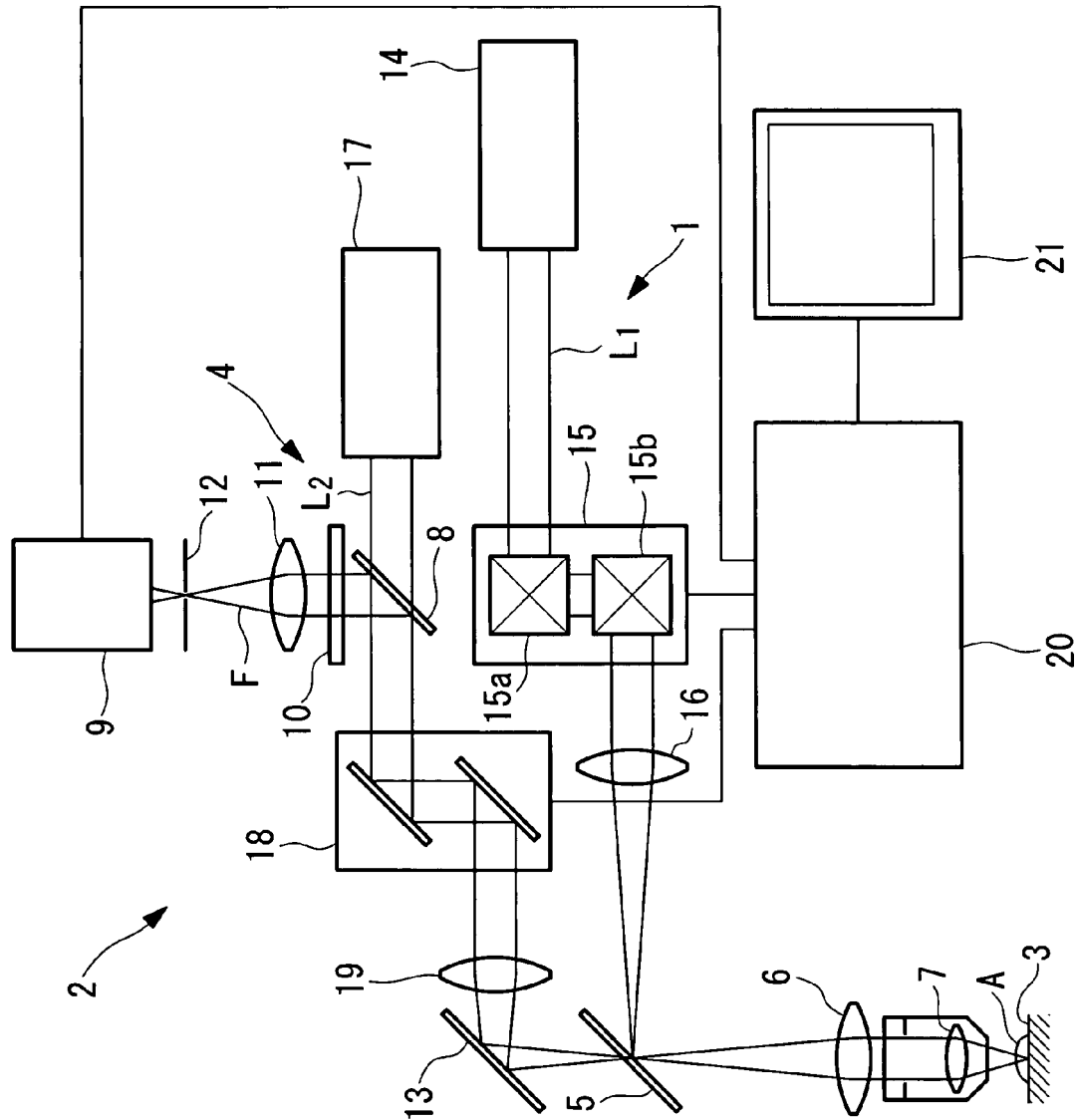
FIG. 1 is a diagram showing the overall configuration of a light-stimulus illumination apparatus and a microscope apparatus according to an embodiment of the present invention.
Figure 2:
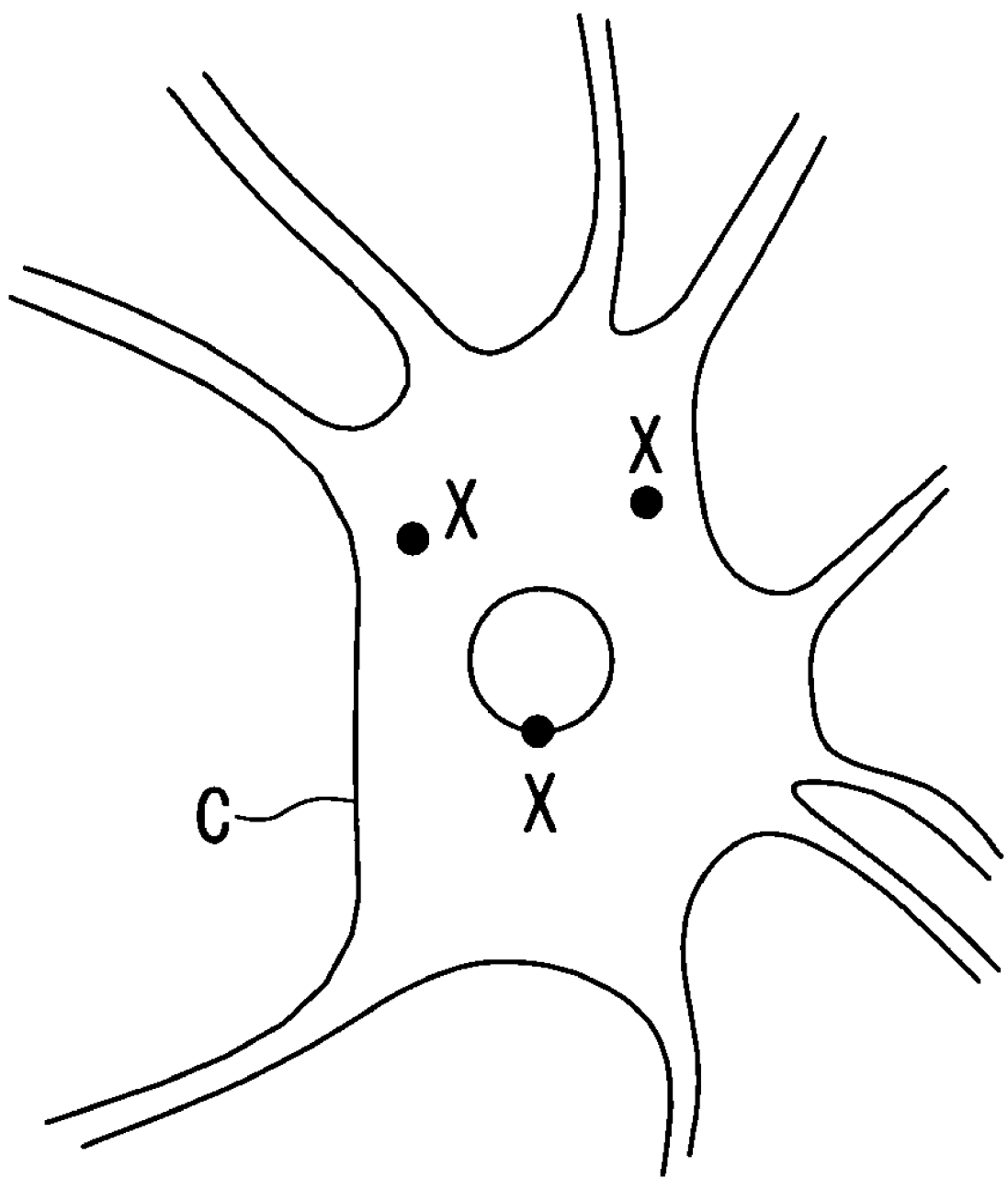
FIG. 2 is a diagram showing an example of light stimulus positions on a specimen to be observed by applying a light stimulus with the light-stimulus illumination apparatus and the microscope apparatus in FIG. 1.

As shown in FIG. 1, a light-stimulus illumination apparatus 1 according to this embodiment is provided in a microscope apparatus 2.

As shown in FIG. 1, the microscope apparatus 2 according to this embodiment includes a stage 3 for mounting a specimen A; the light-stimulus illumination apparatus 1 according to this embodiment; an observation illumination apparatus 4; a beamsplitter 5 for combining light paths of the illumination apparatuses 1 and 4; an image-forming lens 6 for collecting light from the illumination apparatuses 1 and 4, whose light paths were combined, to form substantially collimated light; an objective lens 7 for converging the substantially collimated light to irradiate the specimen A; a dichroic mirror 8 for splitting off fluorescence returning from the specimen A after being collected by the objective lens 7; and a light detector 9 for detecting the split-off fluorescence. Reference numeral 10 in the drawing is a barrier filter, reference numeral 11 is a focusing lens, reference numeral 12 is a pinhole, and reference numeral 13 is a mirror.

The light detector 9 is, for example a photomultiplier tube.

The light-stimulus illumination apparatus 1 according to this embodiment includes a light-stimulus laser light source 14 for emitting light-stimulus laser light $L_1$, a scanner (scanning unit) 15 for two-dimensionally adjusting the beam position in directions orthogonal to the optical axis of the light-stimulus laser light $L_1$ emitted from the light-stimulus laser light source 14, and a pupil projection lens 16 for converging the light-stimulus laser light $L_1$ to form an intermediate image.

The scanner 15 is formed by disposing two acousto-optic devices 15a and 15b, having one-dimensional scanning directions, adjacent to each other such that the scanning directions thereof are orthogonal to each other. Accordingly, switching the frequency of a command signal input to each of the acousto-optic devices 15a and 15b instantaneously changes the scanning position of the light-stimulus laser light $L_1$, and by changing the amplitude of the command signal, it is possible to adjust the intensity of the light-stimulus laser light $L_1$ emerging from the acousto-optic devices 15a and 15b.

The observation illumination apparatus 4 includes an observation laser light source 17 for emitting observation laser light $L_2$, a scanner 18 formed of galvanometer mirrors for two-dimensionally scanning the observation laser light $L_2$ emitted from the observation laser light source 17, and a pupil projection lens 19.

The two acousto-optic devices 15a and 15b constituting the scanner 15 of the light-stimulus illumination apparatus 1, as well as the scanner 18 of the observation illumination apparatus 4, are connected to a controller (control unit) 20. The controller 20 synchronously controls these devices and constructs a fluorescence image by inputting intensity information about the fluorescence acquired by the light detector 9 and associating it with the scanning position of the observation laser light $L_2$ scanned by the scanner 18. The controller 20 is connected to a monitor 21 for displaying the fluorescence image constructed in the controller 20.

The operation of the light-stimulus illumination apparatus 1 and the microscope apparatus 2 according to this embodiment, having such a configuration, will be described below.

To observe the specimen A using the microscope apparatus 2 according to this embodiment, the observation laser light $L_2$ is emitted from the observation laser light source 17 by operating the observation illumination apparatus 4, and the scanner 18 is controlled to two-dimensionally scan the observation laser light $L_2$ by operating the controller 20. After forming an intermediate image with the pupil projection lens 19, the observation laser light $L_2$ passes through the beamsplitter 5, is converted to substantially collimated light by the image-forming lens 6, and is focused by the objective lens 7 to irradiate the specimen A.

Fluorescence F produced by irradiating the specimen A with the observation laser light $L_2$ is collected by the objective lens 7, returns along the same optical path via the image-forming lens 6, the beamsplitter 5, the pupil-projection lens 19, and the scanner 18, is split off from the observation laser light $L_2$ by the dichroic mirror 8, passes through the barrier filter 10, the focusing lens 11, and the pinhole 12, and is detected by the light detector 9. By placing the pinhole 12 in an optically conjugate position with respect to the focal plane of the objective lens 7, only the fluorescence F emitted from the focal position of the objective lens 7 in the specimen A is detected by the light detector 9.

Therefore, the scanning position of the observation laser light $L_2$ scanned by the scanner 18 and the intensity information of the fluorescence F acquired by the light detector 9 are associated with each other in the controller 20, and it is thus possible to display on the monitor 21 a bright fluorescence image of a very thin region extending over the focal plane of the objective lens 7.

With the light-stimulus illumination apparatus 1 according to this embodiment, the scanning position of the light-stimulus laser light $L_1$ emitted from the light-stimulus laser light source 14 is two dimensionally adjusted in directions intersecting the optical axis, with the scanner 15. Then, the light-stimulus laser light $L_1$ irradiates the specimen A via the pupil-projection lens 16, the beamsplitter 5, the image-forming lens 6, and the objective lens 7. By switching the frequency of the command signals input to the two acousto-optic devices 15a and 15b constituting the scanner 15, under the control of the controller 20, it is possible to instantaneously change the scanning position of the light-stimulus laser beam $L_1$ in two dimensions.

As a result, it is possible to apply a light stimulus to a plurality of spatially separated areas within an extremely short time period. In other words, as shown in FIG. 2, for example, it is possible to apply an instantaneous light stimulus to a plurality of points, indicated by reference symbols X, on a cell C. Compared to changing the irradiation position by physically rotating a mirror, as in a conventional galvanometer mirror, because the irradiation position is switched by changing the frequency of the acoustic waves produced in response to the command signal from the controller 20, it is possible to reduce the switching time, allowing the light stimulus to be applied to the plurality of points X substantially simultaneously.

Thus, the microscope apparatus 2 provided with this light-stimulus illumination apparatus 1 affords an advantage in that, by acquiring a fluorescence image of the cell C directly after applying the light stimulus, it is possible to observe an extremely fast response produced in a cell C by the light stimulus.

With the light-stimulus illumination apparatus 1 according to this embodiment, when applying the light stimulus to a plurality of spatially separated regions, it is possible to prevent the light-stimulus laser light $L_1$ from irradiating the areas between these regions. In other words, when applying a light stimulus to regions $S_1$ and $S_2$ that are separated from each other, as shown in FIG. 3, after scanning the light-stimulus laser light $L_1$ in the region $S_1$, the light-stimulus laser light $L_1$ is scanned in the region $S_2$.

Figure 4:
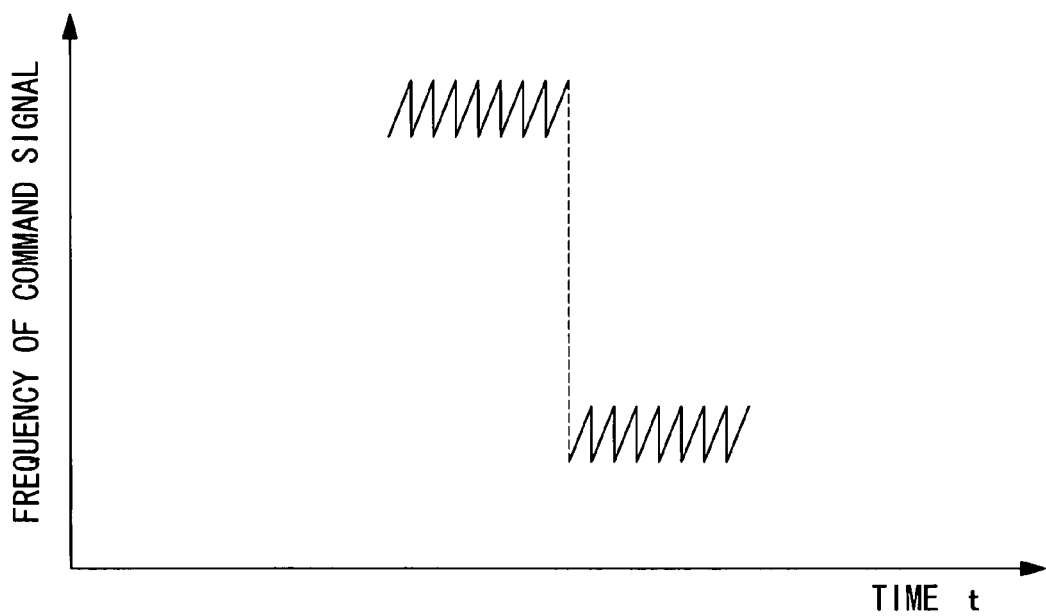
FIG. 4 is a diagram showing an example of a command signal for a scanner when applying the light stimulus to the light stimulus regions shown in FIG. 3.

In this case, as shown in FIG. 4, the frequency of the command signals input to the acousto-optic devices 15a and 15b when moving from the region $S_1$ to the region $S_2$ is switched from a frequency corresponding to a scanning end point of the region $S_1$ to a frequency corresponding to a scanning starting point of the region $S_2$. Accordingly, the diffraction angles of the acousto-optic devices 15a and 15b change discontinuously from the end point of the region $S_1$ to the starting point of the region $S_2$. Thus, when moving from the region $S_1$ to the region $S_2$, the light-stimulus laser light $L_1$ is not radiated between the two regions. By prohibiting radiation of the light-stimulus laser light $L_1$ in the area between the regions $S_1$ and $S_2$ in this way, it is possible to prevent problems such as fading of the specimen A located at the observation region.

In this case, it is not necessary to provide another special device for prohibiting radiation of the light-stimulus laser light $L_1$, which can prevent the apparatus from becoming too complex, and also reduces the cost.

With the light-stimulus illumination apparatus 1 according to this embodiment, by adjusting the amplitude of the command signals input to the acousto-optic devices 15a and 15b according to the scanning positions of each of the acousto-optic devices 15a and 15b constituting the scanner 15, the light-stimulus laser beam $L_1$ is emitted from the scanner 15 with a constant intensity. In other words, because the acousto-optic devices 15a and 15b have characteristics whereby the diffraction efficiency varies as the diffraction angle varies, unless some countermeasure is taken, the intensity of the emitted light-stimulus laser beam $L_1$ varies according to the change in diffraction angle. However, according to this embodiment, it is possible to correct for this effect by adjusting the amplitudes of the command signals input to the acousto-optic devices 15a and 15b, and therefore, it is possible to radiate the light-stimulus laser light $L_1$ with a constant intensity in the plurality of spatially separated regions $S_1$ and $S_2$ and in the regions $S_1$ and $S_2$ having a certain extent.

Even when it is desired to change the intensity of the light-stimulus laser light $L_1$ irradiating the plurality of spatially separated regions $S_1$ and $S_2$, it is possible to easily configure the apparatus by adjusting the amplitudes of the command signals input to the acousto-optic devices 15a and 15b.

In the light-stimulus illumination apparatus 1 according to this embodiment, the scanner 15 is constructed of the two acousto-optic devices 15a and 15b whose scanning directions are set to be orthogonal. Instead of this, however, it is possible to construct a high-speed side using the acousto-optic device 15a and low-speed side using a galvanometer mirror (not shown in the drawing).

In addition, it is possible to emit laser beams with a plurality of wavelengths from the light-stimulus laser light source 14, and it is also possible to provide another acousto-optic device (not shown in the drawing), such as an AOTF, before the scanner 15 to selectively introduce to the scanner 15 only the light-stimulus laser light $L_1$ with a specific wavelength in the light-stimulus laser light $L_1$. In such a case, by synchronously controlling the acousto-optic devices 15a and 15b and the AOTF, it is possible to instantaneously radiate the light-stimulus laser light $L_1$ with a plurality of wavelengths in a plurality of regions.

Figure 5:
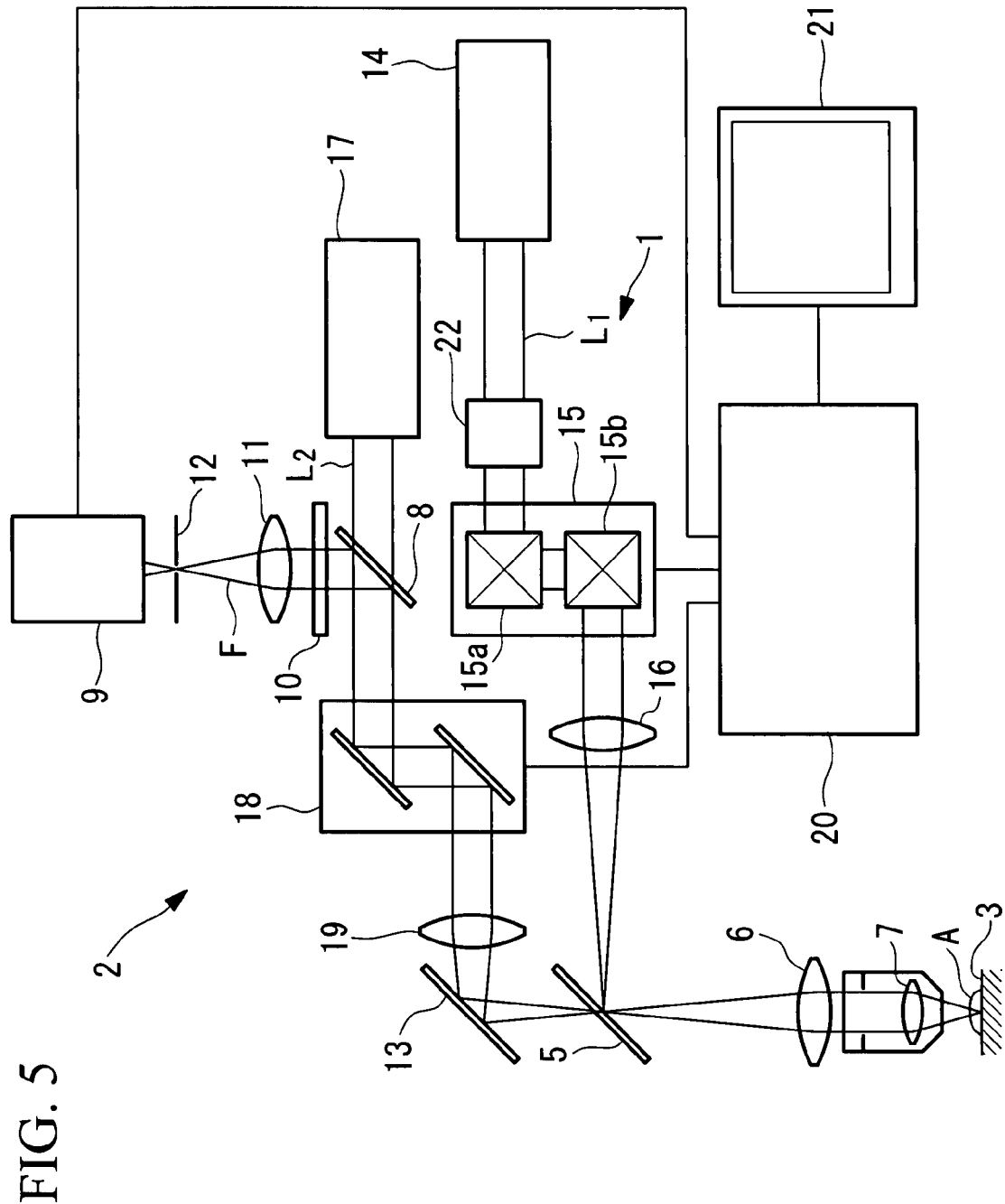
FIG. 5 is a diagram showing the overall configuration of a modification of the light-stimulus illumination apparatus and the microscope apparatus in FIG. 1.

In this embodiment, a description has been given of a case in which the irradiation position of the light-stimulus laser light $L_1$ is varied in two dimensions intersecting the optical axis using the two acousto-optic devices 15a and 15b that scan the light-stimulus laser light $L_1$ in two directions intersecting the optical axis. Instead of this, however, as shown in FIG. 5, it is possible to three-dimensionally vary the irradiation position of the light-stimulus laser light $L_1$ by providing a wavefront conversion device 22 to shift the focal plane of the objective lens 7 in the optical-axis direction.

It is possible to perform light stimulation using a multiphoton absorption phenomenon by employing ultrashort pulsed laser light as the light-stimulus laser light $L_1$. By doing so, it is possible to apply a light stimulus to only an extremely limited region in the optical-axis direction in the vicinity of the focal plane of the objective lens 7.

Figure 6:
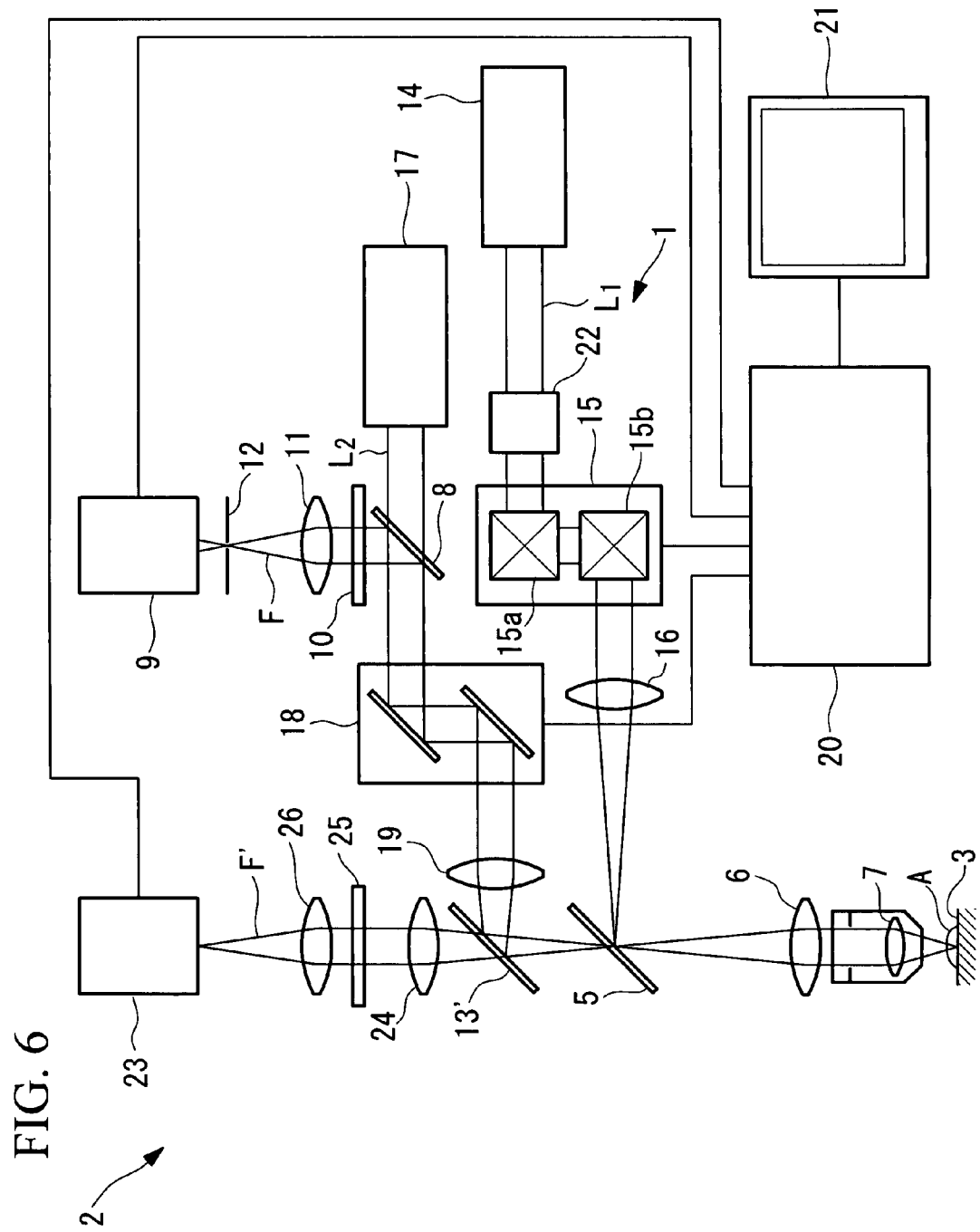
FIG. 6 is a diagram showing the overall configuration of another modification of the light-stimulus illumination apparatus and the microscope apparatus in FIG. 1.

In this case, it is possible to produce a multiphoton-excitation effect in the specimen A using the light-stimulus laser light $L_1$. Thus, as shown in FIG. 6, another light detector 23 is provided for detecting fluorescence F' generated by the multiphoton excitation, which is collected by the objective lens, and split off by a dichroic mirror 13' before returning to the scanner 15. Accordingly, it is possible to detect the fluorescence obtained by scanning the specimen A using the scanner 15, to acquire a multiphoton fluorescence image. In the figure, reference numeral 24 is a pupil-projection lens, reference numeral 25 is a barrier filter, and reference numeral 26 is a focusing lens. In other words, with this configuration, because the fluorescence F' generated by multiphoton excitation is detected before returning to the scanner 15, it is possible to scan the irradiation light with the scanner 15 using an acousto-optic device and to detect fluorescence having a different wavelength from the irradiation light. In this case, the laser light $L_1$ may be observation laser light rather than light-stimulus laser light.

Figure 3:
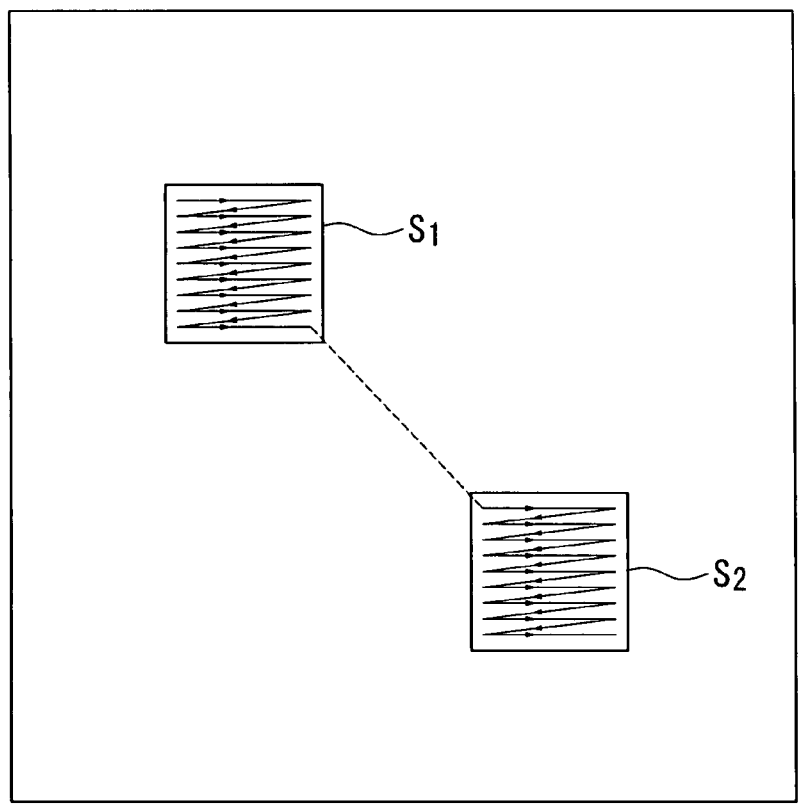
FIG. 3 is a diagram showing an example of light stimulus regions to be observed by applying a light stimulus with the light-stimulus illumination apparatus and the microscope apparatus in FIG. 1.

Regarding the regions $S_1$ and $S_2$ shown in FIG. 3, to irradiate the region $S_2$ a predetermined time interval after irradiating the region $S_1$, the command signal input to the acousto-optic devices in the scanner 15 is first set to zero from a frequency corresponding to an end point of the region $S_1$, and after the predetermined time interval, it is then set to a frequency corresponding to a starting point of the region $S_2$. It is possible to easily realize such control in the present invention because both the on/off state of the laser light and the scanning position setting can be controlled merely with the command signals input to the acousto-optic device.

What is claimed is:

1. A light-stimulus illumination apparatus comprising:
a light source configured to emit light-stimulus laser light;
a scanning unit including a first acousto-optic device configured to scan the light-stimulus laser light emitted from the light source in a first direction intersecting an optical axis, and a second acousto-optic device configured to scan the light-stimulus laser light emitted from the light source in a second direction intersecting the optical axis and orthogonal to the first direction; and
a control unit configured to control the scanning unit so that the light-stimulus laser light irradiates a plurality of spatially separated regions including a first region and a second region in a time-division manner,
wherein the control unit is configured to control the scanning unit to scan the light-stimulus laser light in the second region right after finishing scanning the light-stimulus laser light in the first region by switching a frequency of each command signal input to the first and second acousto-optic devices discontinuously from a frequency corresponding to a scanning end point of the first region to a frequency corresponding to a scanning starting point of the second region so that the light-stimulus laser light does not irradiate an area between the first region and the second region.

2. A light-stimulus illumination apparatus according to claim 1, wherein the control unit adjusts the amplitudes of the command signals input to the first and second acousto-optic devices according to a scanning position of the light-stimulus laser light scanned by the scanning unit.

3. A light-stimulus illumination apparatus according to claim 1, further comprising:
a focal-position adjusting unit configured to change a focal position of the light-stimulus laser light in a direction of the optical axis, wherein the control unit controls the focal-position adjusting unit in synchronization with the scanning unit.

4. A light-stimulus illumination apparatus according to claim 1, wherein the light-stimulus laser light is ultrashort pulsed laser light.

5. A light-stimulus illumination apparatus according to claim 4, further comprising a light detector configured to detect fluorescence due to multiphoton excitation produced by irradiation with the light-stimulus laser light, without the fluorescence returning to the scanning unit.

6. A microscope apparatus comprising the light-stimulus illumination apparatus according to claim 1.

7. A laser-scanning microscope apparatus comprising:
a light-stimulus illumination apparatus according to claim 1; and
a laser-scanning microscope comprising:
an observation light source configured to emit observation laser light;
an observation scanning unit configured to two-dimensionally scan the observation laser light on a specimen;
an objective lens configured to converge the observation laser light on the specimen and to collect observation light emitted from the specimen by irradiation with the observation laser light;
a detection unit configured to detect the observation light collected by the objective lens; and
an image-generating unit configured to generate an observation image of the specimen based on a detection signal from the detection unit,
wherein the light-stimulus laser light irradiates the specimen via the objective lens of the laser-scanning microscope.

8. A laser-scanning microscope apparatus according to claim 7, further comprising:
a combining unit, between the observation scanning unit and the objective lens, configured to combine the light-stimulus laser light from the light-stimulus illumination apparatus,
wherein the light-stimulus laser light scanned by the scanning unit of the light-stimulus illumination apparatus is guided to the combining unit.

* * * * *